United States Patent [19]

DeVries et al.

[11] Patent Number: 4,547,923
[45] Date of Patent: Oct. 22, 1985

[54] SURGICAL KNIFE CLEANER

[75] Inventors: James H. DeVries, Grand Rapids, Mich.; John H. Dufek, Birmingham, Ala.

[73] Assignee: DLP Inc., Grand Rapids, Mich.

[21] Appl. No.: 591,397

[22] Filed: Mar. 15, 1984

[51] Int. Cl.⁴ .................................................. A47L 25/00
[52] U.S. Cl. ....................................... 15/104 R; 15/142
[58] Field of Search .................... 15/104 R, 104.5, 1, 15/142, 236 R; 366/129, 342, 343; 211/120, 45

[56] References Cited

U.S. PATENT DOCUMENTS

| 627,622 | 6/1899 | Meyer | 15/218.1 |
| 977,680 | 12/1910 | Robison | 15/218.1 |
| 2,482,258 | 9/1949 | Funk et al. | 211/120 X |
| 4,011,693 | 3/1977 | Eldridge et al. | 15/218.1 X |
| 4,223,791 | 9/1980 | Taggart | 211/120 |
| 4,308,634 | 1/1982 | Eisenberg | 15/142 |
| 4,418,436 | 12/1983 | Eisenberg | 15/142 X |

Primary Examiner—Chris K. Moore
Attorney, Agent, or Firm—Barnes, Kisselle, Raisch, Choate, Whittemore & Hulbert

[57] ABSTRACT

A surgical knife cleaner and, more particularly, a cleaner for a cautery knife used to clean and cauterize incisions and wounds. A readily attachable base has a cradle to retain a closely coiled strand on an axis parallel to the base. The cradle has edges to limit the introduction of the knife in the direction transverse to the axis of the coil and to clean the edge of the knife.

5 Claims, 4 Drawing Figures

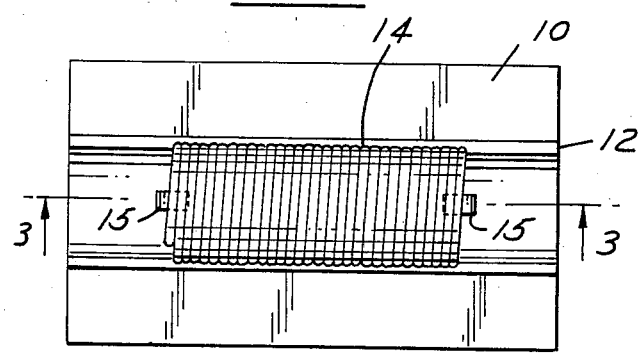
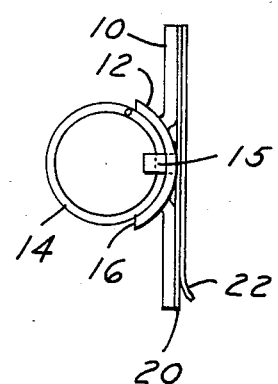
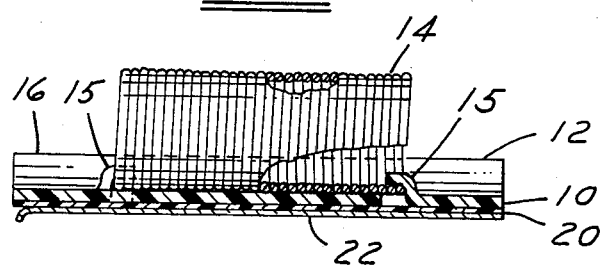
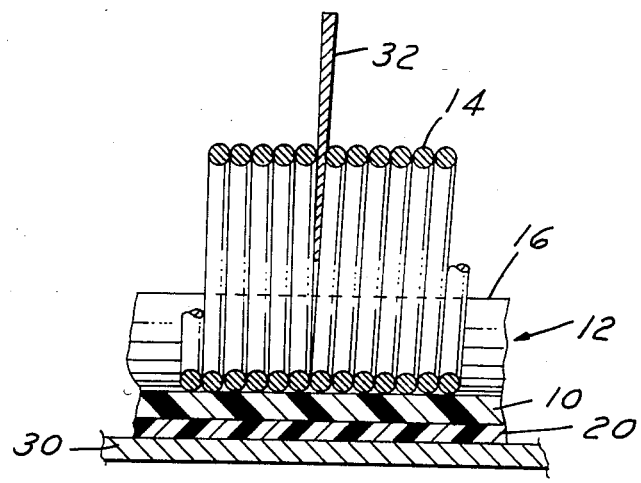

SURGICAL KNIFE CLEANER

FIELD OF THE INVENTION

Cleaning devices for knives used in surgery.

BACKGROUND OF INVENTION

During surgery, cautery knives are used for cauterization as well as cutting, for example, to destroy dead tissue, to stop bleeding and prevent the spread of infection. In this process, the cautery knife accumulates debris and should be frequently cleaned to remove unwanted tissue and maintain a clean incision.

Devices presently used for this purpose comprise sandpaper pads or a single slot molded into the edge of a holster in which the knife is kept.

It is an object of the present invention to provide an improved cautery knife cleaner which is disposable so that the debris which accumulates on the cleaner will not contaminate the knife during re-use. It is a further object to provide a cleaner which can be readily used by the surgeon using only the hand holding the knife. It is a still further object to provide a cleaner which provides a progressive length for cleaning so that a fresh area can be used for each cleaning stroke.

Other objects and features of the invention will be evident in the following description and claims in which the invention is described together with details to enable persons skilled in the art to make and use the device, all in connection with the best mode presently contemplated for the invention.

BRIEF DESCRIPTION OF THE DRAWINGS

Drawings accompany the disclosure and the various views thereof may be briefly described as:

FIG. 1, a plan view of the cautery knife cleaner.

FIG. 2, an end view of the device.

FIG. 3 is a sectional view on line 3—3 of FIG. 1.

FIG. 4, an enlarged view showing a segment of the device in section.

DETAILED DESCRIPTION OF THE INVENTION AND THE MANNER AND PROCESS OF USING IT

With reference to FIG. 1, a plan view of the cautery knife cleaner is illustrated. An end view is shown in FIG. 2. A base plate 10 has an elongate, open-top, receptacle or cradle 12 with a circular cross-section extending the length of the base. These parts can be made separately and joined together at the base of the receptacle or preferably molded of a dense plastic as one piece. The cross-section of the receptacle 12 is preferably semi-circular or slightly larger than semi-circular.

Disposed in the cradle 12 is a coiled spring 14, the coils being disposed adjacent each other in a tight wind, i.e. in physical contact as shown in the drawing. The spring is retained in the cradle 12 by small clips 15 or other equivalent means. The top edges 16 of the cradle lie in a plane below the axis of the spring.

On the underside of the base 10 is a layer of felt with adhesive 20 on both sides which, before use, is covered on the outer side by a protective strip 22.

When the device is to be used, the protective strip 22 is removed to expose the layer of adhesive 20. The knife cleaner can then be secured by the adhesive to any convenient area in the operating area. One location can be the surgical drapes used in the operating room. The device may be located at a place readily accessible to the surgery and used repeatedly for cleaning a cautery knife. In the enlarged view of FIG. 4, the cleaner is shown secured by the adhesive 20 to a surgical drape 30. A cauterization knife 32 is shown in a position as it is being drawn through the adjacent coils of spring 14. The blade of the knife slips easily between the coils of the spring 14 and is drawn over the edges 16 of the cradle 12. Thus, the coils and the edges 16 clean the knife as it is drawn through. In addition, the sides of the cradle support the base of the coil to prevent distortion as the knife is drawn through the coil.

The surgeon may use the coil progressively from one end to the other, thus avoiding areas already used.

While a stainless steel or cadmium plated metal coil 16 can be utilized, it is also possible to use a coiled plastic strand to accomplish a satisfactory cleaning. When an operation is completed, the cleaning device can be disposed of with the surgical drapes. The cost of the device is such that this disposal is more economical than cleaning and the sterilizing the device for use.

What is claimed is:

1. A disposable cleaner for a surgical knife which comprises
   a support base,
   a cradle affixed to and extending along said support base, said cradle having an arcuate cross section with free top edges spaced from said support base,
   a closely wound coil having a central axis,
   means fastening said coil within said cradle, said coil and cradle being dimensioned such that said cradle embraces the lower portion of said coil along its length and such that said cradle and said free top edges simultaneously function to limit insertion of a surgical knife into said coil and to limit lateral motion of said coil relative to said support base, and
   means for removably securing said support base to a surgical operating area.

2. The disposable cleaner set forth in claim 1 wherein said free top edges of said cradle are disposed between said central axis and said support base.

3. The disposable cleaner set forth in claim 2 wherein said fastening means comprises means fastening said coil within said cradle with adjacent turns of said coil in contact.

4. The disposable cleaner set forth in claim 3 wherein said fastening means comprises a pair of clips projecting from said cradle and embracing opposed lower ends of said coil.

5. The disposable cleaner set forth in claim 4 wherein said securing means comprises adhesive means positioned on a side of said support base remote from said cradle.

* * * * *